United States Patent [19]

Jacobsen et al.

[11] Patent Number: 5,833,632
[45] Date of Patent: Nov. 10, 1998

[54] HOLLOW GUIDE WIRE APPARATUS CATHETERS

[75] Inventors: Stephen C. Jacobsen; Clark Davis; David Wells, all of Salt Lake City, Utah

[73] Assignee: Sarcos, Inc., Salt Lake City, Utah

[21] Appl. No.: 729,171

[22] Filed: Oct. 11, 1996

Related U.S. Application Data

[62] Division of Ser. No. 568,493, Dec. 7, 1995.

[51] Int. Cl.[6] ........................................... A61B 5/00
[52] U.S. Cl. ..................... 600/585; 600/373; 606/41; 607/122
[58] Field of Search ............... 604/95; 607/122; 600/373, 585; 606/41

[56] References Cited

U.S. PATENT DOCUMENTS

| | | |
|---|---|---|
| 4,884,579 | 12/1989 | Engelson . |
| 4,955,862 | 9/1990 | Sepetka . |
| 4,994,069 | 2/1991 | Ritchart et al. . |
| 5,304,131 | 4/1994 | Paskar . |
| 5,438,993 | 8/1995 | Lynch et al. . |
| 5,441,483 | 8/1995 | Avitall . |
| 5,441,489 | 8/1995 | Utsumi et al. . |

FOREIGN PATENT DOCUMENTS

PCT/US92/07619  9/1992  WIPO .

*Primary Examiner*—Mark Bockelman
*Attorney, Agent, or Firm*—Thorpe North & Western, LLP

[57] ABSTRACT

A catheter guide wire includes an elongate tubular body about which a catheter may be threaded for guidance to a target location in a vasculature passageway of a body. The elongate body includes a proximal end and a distal end, with the distal end being curved. Cuts are formed either by saw-cutting, laser cutting or etching at spaced-apart locations along the length of the body to increase its lateral flexibility, while maintaining its rotational torquability. At least some of the cuts extend through the tubular body to the interior cavity to allow the escape of fluids flowing in the cavity. The distal end of the tubular body includes a sufficient number of cuts to make it more flexible than the remainder of the body.

2 Claims, 2 Drawing Sheets

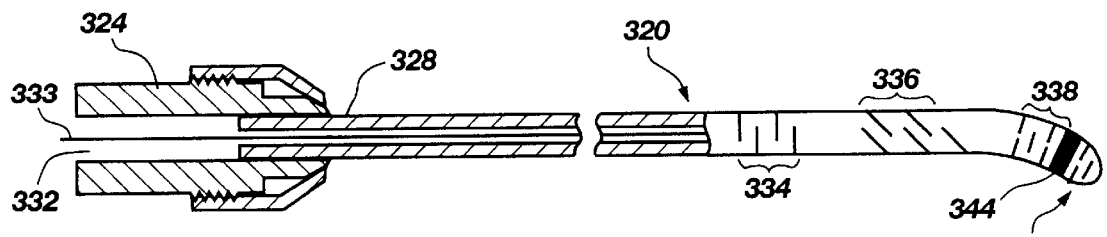
Fig. 1
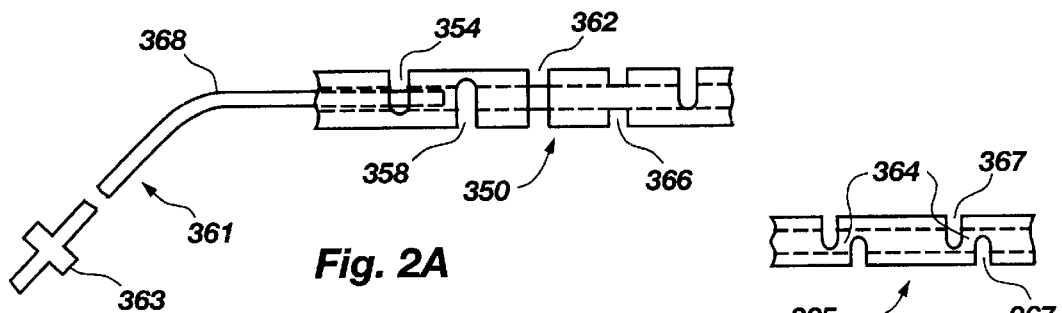
Fig. 2A
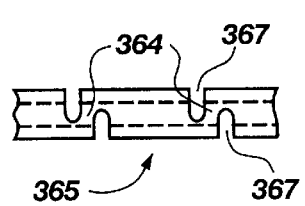
Fig. 2B
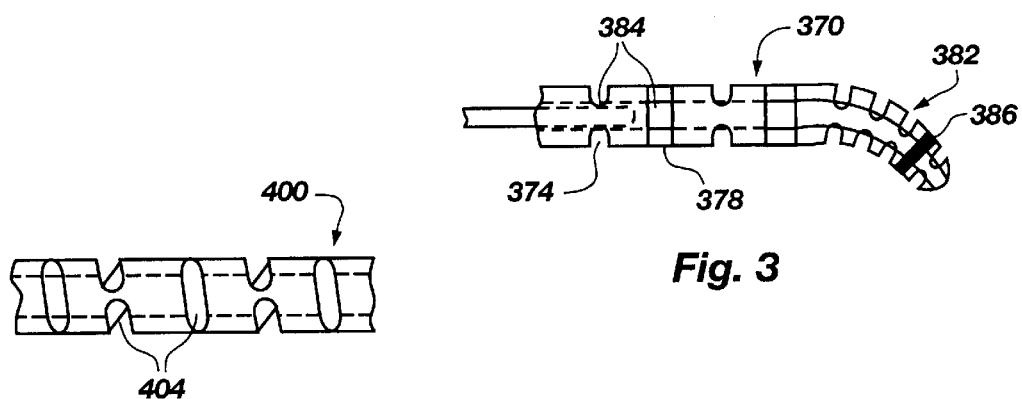
Fig. 3
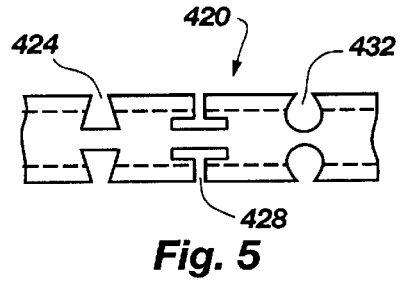
Fig. 4A
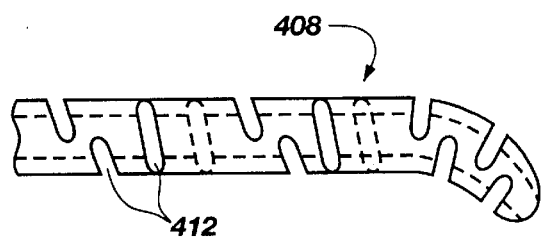
Fig. 4B
Fig. 5

HOLLOW GUIDE WIRE APPARATUS CATHETERS

This application is a divisional of application Ser. No. 08/568,493, filed Dec. 7, 1995, pending.

BACKGROUND OF THE INVENTION

This invention relates to catheter systems and more particularly to hollow guide wire apparatus with improved torque and flexure characteristics.

Catheter guide wires have been used for many years to "lead" or "guide" catheters to desired target locations in the human body's vasculature. The typical guide wire is from about 135 centimeters to 195 centimeters in length, and is made from two primary pieces —a stainless steel solid core wire, and a platinum alloy coil spring. The core wire is tapered on the distal end to increase its flexibility. The coil spring is typically soldered to the core wire at its distal end and at a point where the inside diameter of the coil spring matches the outside diameter of the core wire. Platinum is selected for the coil spring because it provides radiopacity for X-ray viewing during navigation of the guide wire in the body, and it is biocompatible. The coil spring also provides softness for the tip of the guide wire to reduce the likelihood of puncture of the anatomy.

Navigation through the anatomy is achieved by viewing the guide wire in the body using X-ray fluoroscopy. The guide wire is inserted into a catheter so the guide wire protrudes out the end, and then the wire and catheter are inserted into a vessel or duct and moved therethrough until the guide wire tip reaches a desired vessel or duct branch. The proximal end of the guide wire is then rotated or torqued to point the curved tip into the desired branch and then advanced farther. The catheter is advanced over the guide wire to follow or track the wire to the desired location, and provide additional support for the wire. Once the catheter is in place, the guide wire may be withdrawn, depending upon the therapy to be performed. Oftentimes, such as in the case of balloon angioplasty, the guide wire is left in place during the procedure and will be used to exchange catheters.

As the guide wire is advanced into the anatomy, internal resistance from the typically numerous turns, and surface contact, decreases the ability to advance the guide wire farther. This, in turn, may lead to a more difficult and prolonged procedure, or, more seriously, failure to access the desired anatomy and thus a failed procedure. A guide wire with both flexibility and good torque characteristics (torsional stiffness) would, of course, help overcome problems created by the internal resistance.

SUMMARY OF THE INVENTION

It is an object of the invention to provide an improved catheter guide wire apparatus.

It is also an object of the invention to provide such apparatus which exhibits both torsional stiffness, bending flexibility, and longitudinal strength. It is a further object of the invention to provide such apparatus which is simple in design and construction, and allows for selectively varying the bending flexibility of the apparatus along the length thereof.

The above and other objects of the invention are realized in a specific illustrative embodiment of a catheter guide wire is formed of a thin, elongate, hollow tubular body of material, the exterior surface of which includes a plurality of cuts spaced apart along at least a portion of the length of the body. The cuts extend transversely of the body and are positioned to give the guide wire flexibility without significantly reducing torsional stiffness. With this embodiment, the guide wire, being hollow, may serve also as a catheter itself.

BRIEF DESCRIPTION OF THE DRAWINGS

The above and other objects, features and advantages of the invention will become apparent from a consideration of the following detailed description presented in connection with the accompanying drawings in which:

FIG. 1 is a side, fragmented, partially cross-sectional view of a tubular guide wire formed with cuts, in accordance with the present invention;

FIGS. 2A, 2B and 3 show side, fragmented views of three embodiments of a tubular guide wire formed with cuts, in accordance with the present invention;

FIGS. 4A and 4B are side, fragmented views of other embodiments of a tubular guide wire formed with cuts, in accordance with the present invention;

FIG. 5 is a side, fragmented view showing two different types of cuts or etchings which may be utilized in a hollow guide wire in accordance with the present invention;

DETAILED DESCRIPTION

Figure 6:
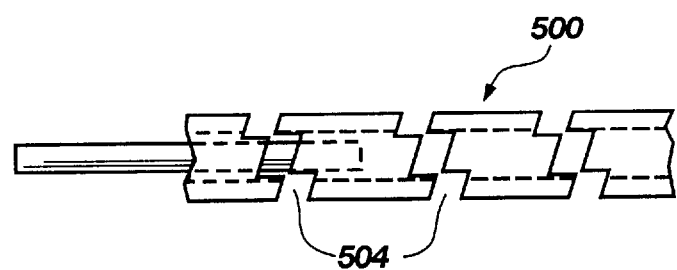
FIG. 6 is a side, fragmented view of still another embodiment of a tubular guide wire etched or cut to form interlocking teeth, in accordance with the present invention.

FIG. 1 is a side, fragmented, partially cross-sectional view of a tubular guide wire 320 made in accordance with the present invention. A pin vise type torquing chuck 324 is shown attached to a proximal end 328 in the usual manner. The chuck 324 also includes an opening, bore, or luer adapter 332 to allow for introduction of medications into the interior of the tubular guide wire 320.

Insertable in the hollow of the tubular guide wire 320 is a wire mandrel 333 which may be made radiopaque to X-ray fluoroscopy or, if magnetic resonance imaging (MRI) were used, the wire mandrel 333 could be made of a material active for MRI detection such as gadolinium or gadolinium compound, gadolinium encapsulated in a sheath, dysprosium, or dysprosium encapsulated in a sheath. Alternatively, a radiopaque solution could be introduced into the interior of the tubular guide wire 320 or a solution visible in MRI could be used, if MRI rather than X-ray fluoroscopy were utilized. The purpose of such a wire mandrel or solutions, of course, would be to allow tracking location and/or movement of the guide wire 320 as it is threaded into vasculature or body cavities.

The wire mandrel 333 could also be used to change the curvature of the tubular guide wire 320 as desired by the user. For example, the tubular guide wire 320 could be formed with a portion of it curved or angled (such as the curved distal end 340 to be discussed momentarily) and a straight wire mandrel 333 could then be inserted into the guide wire to straighten it out and then removed when desired to allow the guide wire to resume the curved shape. Alternatively, the tubular guide wire 320 could be formed to be straight and the wire mandrel 333 formed with selected curves so that when the mandrel were inserted into the tubular guide wire, the mandrel would cause the guide wire to assume those same curves and when the mandrel were removed, the guide wire would again straighten. In this manner, depending upon the initial shape of the wire mandrel 333 and/or the tubular guide wire 320, the shape of the guide wire can be controlled to a certain extent while disposed in vasculature or body cavities.

Advantageously, the tubular guide wire 320 is constructed of nickel titanium alloy and may range in size from about 0.008 inches to 0.090 inches in outside diameter, and about 0.005 inches to 0.084 inches in inside diameter, and about 175 to 300 cm in length. The tubular guide wire 320 could also be made of stainless steel, polymers or other flexible materials having suitable strength.

Cuts, slots, gaps or openings 334, 336 and 338 are formed in the tubular guide wire 320 along the length thereof, either by saw cutting (e.g. diamond grit embedded semiconductor dicing blade); electron discharge machining, laser cutting or etching (for example using the etching process described in U.S. Pat. No. 5,106,455) anisotropically to provide for lateral flexibility in the guide wire. Cuts 334 are generally perpendicular or crosswise to the long dimension of the guide wire and are shown as being cut on alternate sides of the guide wire. (Various cut patterns will be discussed in more detail later.) Cuts 336 are angled to allow for a longer cut, and cuts 338, on the distal end 340 of the guide wire, are also formed perpendicular to the guide wire. Controlling and varying both the spacing and depth of the cuts allows for selection of the flexure profile of the tubular guide wire, the more closely spaced the cuts and the greater depth thereof giving rise to a more flexible guide wire, and vice-versa.

The distal end 340 of the guide wire may be preshaped with a curve, as shown, to allow for directing the guide wire around curves and bends. The cuts 338 allow for maintaining the flexibility in the distal end 340. Advantageously, the tip is rounded to minimize the chance of traumatic piercing of body tissue. Also formed on the distal end 340 may be a radiopaque or MRI marker or band 344. The band 344 may be gold or platinum alloy (for X-ray fluoroscopy) or gadolinium or dysprosium, or compounds thereof (for MRI), and may be formed on the distal end 340 by deposition, wrapping or use of the shape memory alloy (NiTi) effect to "lock" the band around the end. Alternatively, a radiopaque plug may be disposed in the lumen at the distal end 340 (or an MRI marker).

FIG. 2A is a side, fragmented view of a tubular guide wire 350 formed with perpendicular cuts 354, 358, 362, 366, etc., along the length thereof. The cut 354 is formed on the top of the guide wire 350, the cut 358 is formed on the bottom, the cut 362 is formed on the near side of the guide wire, and the cut 366 is formed on the far side. In effect, each cut is rotated by 180 degrees or 90 degrees, and offset from the preceding cut. Of course, the cuts could be formed to provide preferential bending (flex) in one plane, or could be randomly formed to allow bending (flex) equally, non-preferentially in all planes. This could be achieved, for example, by circumferentially spacing the cuts.

FIG. 2B is a side, fragmented view of a tubular guide wire 365 formed with pairs of cuts 367 formed on opposite sides of the guide wire and staggered or offset.

The flexibility (bending stiffness), strength and torsional stiffness of the guide wire are determined primarily by the dimensions and flexure properties of beams formed by the cuts, i.e., the area between opposing cuts (for opposing cuts) or the area between adjacent cuts (for offset cuts). These properties, in turn, are determined by the depth, widths and separation of cuts. Very flexible sections with opposed cuts (such as shown in FIG. 3) generally require that the cuts be deep and/or wide, to yield flexible beams 384. However, it is sometimes difficult to precisely control the depth of cuts without overly weakening the guide wire; and especially wide cuts are impractical because they may cause the guide wire to catch or snag on body tissue. Very flexible sections with offset cuts (such as shown in FIGS. 2A and 2B) may be achieved by reducing the spacing between the cuts to yield flexible beams 364 (FIG. 2B), and this is more accurately controlled than are cut depths, as already discussed. Thus, the use of offset cuts allows for accurately controlling the flexibility of guide wires without the attendant risk of overly weakening them. Disposed in the tubular guide wire 350 is a solid wire mandrel 361 having a bend 368, which will cause the tubular guide wire 350 to conform to the same bend, as previously discussed. The solid wire mandrel 361 provides stiffening for the tubular guide wire 350 for that portion in which the mandrel is inserted. A stop 363 is located at the proximal end of the mandrel 361 to prevent movement of the mandrel, and in particular the distal end of the mandrel, beyond a certain point in the guide wire 350, for example, to avoid puncturing tissue beyond the distal end of the guide wire by the distal end of the mandrel. Further, the mandrel 361 could have a tapered, and thus more flexible, distal end, along with (or without) a blunt or dulled tip.

FIG. 3 is also a side, fragmented view of a tubular guide wire 370, also with cuts 374, 378, etc. formed therein. Cut 374 is actually two cuts formed on the top and the bottom of the guide wire 370, whereas cut 378 comprises two cuts formed on the near side and the far side, etc. A distal end 382 of the guide wire 370 is curved, and includes a radiopaque or MRI band 386. (The distal ends of the guide wires can also be shapeable by the clinician by heating and/or bending.

FIGS. 4A and 4B show a side, fragmented views of a tubular catheter 400 having opposed cuts 404 formed at an angle with the long direction of the guide wire, and tubular guide wire 408 having offset cuts 412 formed at an angle with the long direction of the guide wire, respectively.

FIG. 5 is a side, fragmented view of a tubular guide wire 420, showing three alternative type cuts 424, 428 and 432. These type cuts provide a kind of built-in flexure stop to prevent further flexure of the guide wire 420 when the cut openings close to contact one another and prevent further flexure in that direction. The cuts 424 are formed on opposite sides of the guide wire 420 and are wedge or triangle-shaped, with the greater width of the wedge being at the bottom of the cut. The cuts 428 are likewise formed on opposite sides of the guide wire 420 in the form of T's, with the crosspiece of the T being at the bottom of the cut. The cuts 432 are generally circular as shown. Other cut shapes could also be provided to meet the needs of the user.

FIG. 6 is a side, fragmented view of a tubular guide wire 500 having cuts or etchings 504 which may extend all the way through the guide wire to separate it into pieces, with the cuts or etchings being formed with teeth which interlock when the guide wire is reassembled. When the guide wire is inserted into a vasculature passageway, the teeth in the cuts 504 interlock to prevent relative rotation thereof but also allow significant lateral flexibility.

The tubular guide wire disclosed can be used with a catheter threaded thereover in a conventional manner, or can be used to deliver medication to a target location in a manner similar to the catheters themselves. With cuts formed along the length or at least a portion of the length of the tubular guide wires, the medication is allowed to leak from the bore of the guide wire out into the vasculature passageway. Of course, the location of discharge of medication from the tubular guide wire can be controlled by controlling depth of the cuts as well as the location thereof. In addition, a polymer sleeve may be inserted in the lumen or bore of a tubular guide wire, and/or on the outside as well, for sealing and preventing the outflow or discharge of medication from the guide wire lumen. Controlling the length of such sleeves on the guide wire enables control of discharge points of medication from the guide wire. In addition, a stiffening mandrel or wire can be inserted through the bore or lumen of a tubular guide wire as already discussed, and such mandrel or wire can be curved at selected locations such as location 368 in the mandrel 350 of FIG. 2, to cause a corresponding bend in the tubular guide wire. Alternatively, the tubular guide wire can be formed with one or more bends and then a substantially straight mandrel may be inserted into the hollow of the guide wire to cause it to straighten as needed. Also, the mandrel can be made of a material so that it is visible either with X-ray fluoroscopy or MRI, depending upon the process used to view the clinical procedure.

Figure 7:
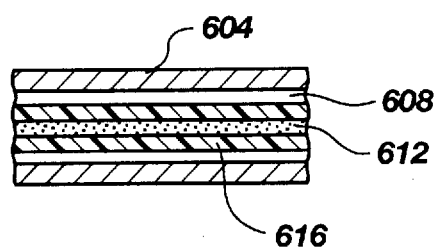
FIG. 7 is a side, fragmented view of a metal tubular guide wire or catheter, with central metal conductor, suitable for use in making electrical measurements, applying electromagnetic signals to the body, etc.

FIG. 7 is a side, cross-sectional, fragmented view of a tubular catheter guide wire 604 made from a metallic or other electrically conductive alloy, in the lumen 608 of which is disposed an electrically conductive wire 612 about which is disposed an electrically insulative sheath 616. Alternatively, the interior wall of the lumen 608 could include a layer of insulation and obviate the need for the insulative sheath 616. Illustratively, the diameter of the lumen 608 could be 0.009 inches, and the diameter of the wire 612 and sheath 616 could be 0.006 inches.

The structure of FIG. 7 illustrates a use of the tubular catheter/guide wire of the present invention for making internal electrical measurements such as the detection of voltage patterns at a target location in the body. Also, the combination of FIG. 7 could be used for ablation in which a radio frequency or other signal is transmitted over the conductor tube 604 and conductor wire 612 to the distal end to tissue in front of the distal end. In addition, a heating coil could join the tubular conductor 604 and the conductor wire 612 at the distal end to provide a heating element for performing thermal treatment at a target location in the body. Of course, other electrical measurements or treatments could be utilized with the structure of FIG. 7. Of course, the typical guide wires discussed earlier, being solid, could not provide this function, nor could typical catheters since they are made of non-metallic material.

In the embodiments of the guide wire discussed above, the guide wires can be made "flow directable" by providing highly flexible distal ends. "Flow directability" means that the distal end of the guide wire tends to "flow" with the blood around curves and bends in a vasculature passageway. To reduce resistance to movement of a guide wire in a vasculature passageway, the surface of the guide wire may be electropolished to increase the smoothness thereof, and additionally, a lubricious coating may be applied to the surface of the guide wire —such coatings might illustratively include silicone based oil and/or polymer or hydrophilic polymers. Alternatively, a lubricous sleeve made, fore example, of a hydrophilic polymer could also be provided for disposal of the guide wire.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A catheter conductor pair comprising:

an electrically conductive catheter for introduction into a vessel pathway of a body, the catheter having an exterior surface made of electrically conductive material which includes a plurality of cuts spaced apart along at least a portion of the length of the electroconductive material to increase lateral flexibility of the catheter, and an electrically conductive wire disposed in the lumen of the catheter and generally co-extensive therewith and insulative material between said electrically conductive wire and said electrically conductive material, said electrically conductive wire for carrying electrical signals, in conjunction with the catheter, along the co-extensive length thereof.

2. A catheter conductor pair as in claim 1, further comprising an electrically insulative sleeve disposed about the electrically conductive wire to prevent electrical shorting between the wire and catheter.

* * * * *